United States Patent [19]

Baylink

[11] Patent Number: 5,330,410
[45] Date of Patent: * Jul. 19, 1994

[54] METHOD FOR INCREASED PRODUCTION OF GROWTH FACTOR IN LIVING TISSUE USING AN APPLIED FLUCTUATING MAGNETIC FIELD

[75] Inventor: David J. Baylink, Redlands, Calif.

[73] Assignee: IatroMed, Inc., Phoenix, Ariz.

[*] Notice: The portion of the term of this patent subsequent to Mar. 23, 2010 has been disclaimed.

[21] Appl. No.: 14,968

[22] Filed: Feb. 8, 1993

Related U.S. Application Data

[63] Continuation of Ser. No. 718,455, Jun. 20, 1991, Pat. No. 5,195,940.

[51] Int. Cl.⁵ .............................................. A61N 2/04
[52] U.S. Cl. .................................................... 600/13
[58] Field of Search .................................. 600/13–15; 128/419 F

[56] References Cited

U.S. PATENT DOCUMENTS

| | | | |
|---|---|---|---|
| 3,890,953 | 6/1975 | Kraus et al. | 128/419 F X |
| 3,893,462 | 7/1975 | Manning | 128/421 |
| 4,105,017 | 8/1978 | Ryaby et al. | 128/419 F X |
| 4,266,532 | 5/1981 | Ryaby et al. | 128/419 F X |
| 4,428,366 | 1/1984 | Findl et al. | 128/804 X |
| 4,548,208 | 10/1985 | Niemi | 128/419 F |
| 4,561,426 | 12/1985 | Stewart | 127/419 F |
| 4,616,629 | 10/1986 | Moore | 128/419 F |
| 4,622,952 | 11/1986 | Gordon | 604/20 X |
| 4,622,953 | 11/1986 | Gordon | 604/20 X |
| 4,654,574 | 3/1987 | Thalor | 320/14 |
| 4,683,873 | 8/1978 | Cadossi et al. | 128/419 F |
| 4,818,697 | 4/1989 | Liboff et al. | 435/173 |
| 4,871,718 | 10/1989 | Carniglia | 514/23 |
| 4,932,951 | 6/1990 | Liboff et al. | 128/419 F X |
| 5,123,898 | 6/1992 | Liboff et al. | 600/13 |
| 5,195,940 | 3/1993 | Baylink | 600/14 |

FOREIGN PATENT DOCUMENTS

38255 1/1985 Australia .
1113156 11/1981 Canada .

OTHER PUBLICATIONS

Liboff, "Geomagnetic Cyclotron Resonance in Living Cells," Journal of Biological Physics, vol. 13, 1985.
Liboff, "Cyclotron Resonance in Membrane Transport," Interactions between Electromagnetic Fields and Cells (1985).
Blackman, et al. "A Role for the Magnetic Field in the Radiation Induced Efflux of Calcium Ions from Brain Tissue in Vitro," Bioelectromagnetics vol. 6327 (1985).

*Primary Examiner*—Francis Jaworski
*Attorney, Agent, or Firm*—Dykema Gossett

[57] ABSTRACT

A method for stimulating the production of growth factor in living tissue is provided. The method involves time application of a controlled, fluctuating, directionally oriented magnetic field parallel to a predetermined axis projecting through the target tissue. This method provides a non-invasive technique for mediating tissue growth, maintenance, and repair by stimulating the production of growth factors in the tissue of interest. Because cell growth is stimulated by increased levels of growth factor (such as, for example, insulin-like growth factor-II) the beneficial effect remains and continues after the applied magnetic field is removed. Increases in the production of growth factor in the range of 20 to 50 percent have been observed.

4 Claims, 3 Drawing Sheets

METHOD FOR INCREASED PRODUCTION OF GROWTH FACTOR IN LIVING TISSUE USING AN APPLIED FLUCTUATING MAGNETIC FIELD

This is a continuation of copending application Ser. No. 07/718,455 filed on Jun. 20, 1991 now U.S. Pat. No. 5,195,940.

FIELD OF THE INVENTION

The present invention relates generally to methods and apparatus for stimulating the production of growth factors in living tissue. More specifically, the present invention relates to non-invasive techniques for stimulating the production of growth factors in the tissue of interest.

BACKGROUND OF THE INVENTION

In recent years, multidisciplinary investigations of developmental processes have provided evidence suggesting that electric and magnetic fields play an important role in cell and tissue behavior. In U.S. Pat. No. 4,818,697, entitled, "Techniques for Enhancing the Permeability of Ions," the disclosure of which is incorporated herein by reference, a method and apparatus are disclosed by which transmembrane movement of a preselected ion is magnetically regulated using a time-varying magnetic field. The fluctuating magnetic field is tuned to the cyclotron resonance energy absorption frequency of the preselected ion. And in U.S. Pat. No. 4,932,951, entitled "Method and Apparatus for Controlling Tissue Growth and An Applied Fluctuating Magnetic Field," the disclosure of which is incorporated herein by reference, a method and apparatus are disclosed whereby the growth characteristics of target tissue can be influenced by exposing the target tissue, especially bone tissue, to a magnetic field with precise predetermined ratios of frequency to average magnetic flux density. These important discoveries brought to light the interplay of local geomagnetic fields and frequency dependence in ion transport mechanisms.

In the present invention, a magnetic field is used to stimulate the production of growth factor in vivo. The growth factors produced can, by stimulating cell growth and cell replication, exert a beneficial and continuing influence after removal of the magnetic field.

Growth factors have long been recognized as potent molecules that can increase the proliferation of many cellular types of living tissue. These growth factors have been identified and produced in-vitro. The problems associated with the delivery of the in-vitro produced growth factor to a specific site in a living organism has limited the use of growth factors as a therapeutic tool.

It has now been found that the production of growth factor can be increased in vivo by the exogenous stimulation of living tissue with magnetic fields. In effect, the existing cells are stimulated to increase the intracellular synthesis of growth factor and/or decrease the intracellular synthesis of growth factor inhibitors by the applied magnetic field. The net effect is an increase in the amount of effective growth factor available to influence cell growth and proliferation and, therefore, a net increase in the amount of mitogenic cellular activity. The increased level of growth factor, in turn, results in increased levels of cell production and proliferation. This increased rate of cell growth results in increased rates of cell repair, regeneration and/or remodeling in the local area of interest. When applied to a damaged area of tissue, the present invention allows for an increased rate of repair or healing using the cells' natural regenerating and repair capabilities.

SUMMARY OF THE INVENTION

The present invention provides a method by which the production of growth factor within living tissue can be increased or stimulated in vivo by the application of magnetic fields to the living tissue of interest. By increasing the production of naturally occurring growth factor, the rate of cell growth and repair can be increased with minimal side effects. In addition, by increasing the production of growth factor in vivo, the effectiveness and efficiencies of the growth factor is maximized.

One object of the present invention is to provide a method for stimulating the product of growth factor in living tissue, where the method comprises the steps of:
(a) positioning a magnetic field generating means adjacent the living tissue, where the living tissue is subject to an ambient magnetic field flux;
(b) generating an applied magnetic flux with the magnetic field generating means such that the applied magnetic field flux extends through the living tissue along an axis and combines with the ambient magnetic field to form a composite magnetic flux; and
(c) fluctuating the applied magnetic flux and controlling the average value of the magnetic flux density of the combined magnetic flux to create and maintain a relationship between the frequency of the fluctuations and the average value of the combined magnetic flux density, wherein the average value of the combined magnetic flux density is a non-zero average value, wherein the relationship stimulates the production of growth factor in the living tissue, and wherein the relationship between the frequency of the fluctuations and the average value of the combined magnetic flux density is a function of $$f_c = (B/2\pi)(q/m)$$

wherein $f_c$ is the frequency in Hertz, B is the non-zero average value of the combined magnetic field flux density in Tesla, and q/m is the charge to mass ratio of an ionic species in Coulombs/kilograms.

Another object of the present invention is to provide a method for stimulation of the production of growth factor in tissue within a human subject in an ambient magnetic field, where the method comprises the steps of:
(a) generating an oscillating applied magnetic flux along an axis through a region of the tissue to be stimulated in a human subject with a pair of field coils, the field coils being placed in opposed relation adjacent the tissue to be stimulated such that the oscillating applied magnetic flux combining with the ambient magnetic flux extends through the tissue to be stimulated along the axis thereby forming an oscillating composite magnetic field;
(b) periodically measuring the average value of the magnetic flux density of the combined magnetic field extending through the tissue to be stimulated along the axis with a magnetic field sensor positioned adjacent the tissue to be stimulated; and
(c) adjusting the ratio of the frequency of oscillation of the oscillating composite magnetic field along the axis to the average value of the magnetic flux density of the composite magnetic field, wherein the average value of the magnetic flux density of the composite magnetic field extending through the tissue to be stimulated along the axis is a non-zero value and wherein the ratio is a function of the charge-to-mass ratio of an ion present in the tissue to be stimulated, whereby the composite magnetic field with its adjusted ratio stimulates the production of growth factor in the tissue.

Other objects and advantages of the present invention will be apparent from a consideration of this specification, including the appended claims and accompanying drawings.

DETAILED DESCRIPTION OF PREFERRED EMBODIMENTS

Figure 1:
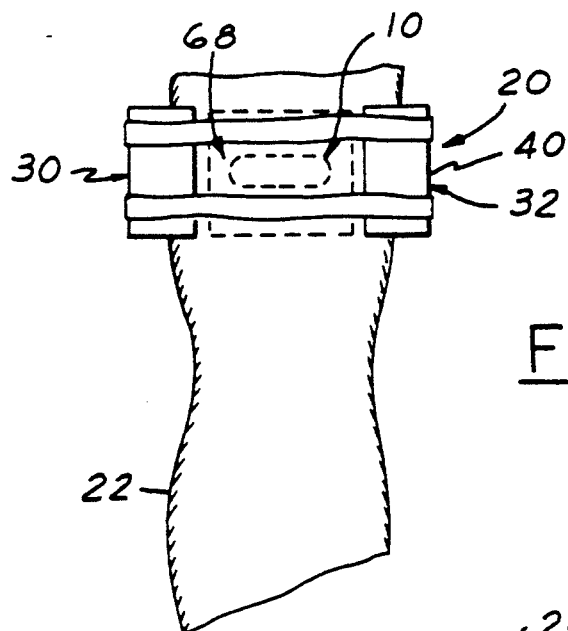
FIG. 1 is a front elevational view of the present invention as applied to the treatment of a injured leg.

The present invention provides a method of stimulating the growth factor production of living tissue in vivo and thereby influencing the growth characteristic of the living tissue. This is achieved by generating a fluctuating, directionally-oriented magnetic field which projects through the target tissue.

A number of magnetic field generating means are suitable for this purpose, but the apparatus disclosed in the foregoing U.S. Pat. Nos. 4,818,697 and 4,932,951 are particularly preferred. The magnetic field so generated has a magnetic flux density of precisely controlled parameters which passes through the target tissue parallel to a predetermined axis projecting through the tissue. As will be known by those skilled in art and as is clearly explained, the local magnetic field to which the target tissue is subjected will have a component which is parallel to the predetermined axis and which thus aids or opposes the applied or generated magnetic field along the axis. At times, the local component may be zero. In the method of the present invention, the density of this combined magnetic flux, and more specifically the average non-zero value of the combined magnetic flux density, is controlled to provide a precise relationship between the flux density along the axis and the frequency of the applied magnetic field which is oscillating at a predetermined value. Most preferably this is accomplished by adjusting the intensity of the applied field to compensate for changes in the local field. Thus, in one embodiment, the present invention provides a method of stimulating growth factor production of living tissue by creating a magnetic field which penetrates the tissue and which has a predetermined relationship between frequency of oscillation and average flux density. The predetermined relationship or ratio of frequency-to-field magnitude is determined with reference to the equation:

$$f_c = (B/2\pi)(q/m)$$

where $f_c$ is the frequency of the combined magnetic field along the predetermined axis in Hertz, B is non-zero net average value of the magnetic flux density of the combined magnetic field parallel to the axis in Tesla, q/m is the charge to mass ratio of a preselected ionic species associated with the production of growth factor and is in units of Coulombs per kilogram. Generally, q/m is from about $5 \times 10^5$ to about $100 \times 10^6$ Coulombs/kg and B preferably has a value not in excess of about $5 \times 10^{-4}$ Tesla.

In order to create this fluctuating magnetic field having the desired parameters, the composite magnetic field parallel to the predetermined axis is constantly monitored. As discussed more fully below, this is preferably carried out with a Hall effect device or the like which produces an analog signal. This analog signal is periodically sampled by microprocessing means which then calculates the necessary frequency and/or magnitude of the applied magnetic field to maintain the preprogrammed, predetermined ratio previously described. It is the combined magnetic flux which is sensed by the magnetic field sensor. The magnetic field generating means is used to adjust the magnitude of this composite field where appropriate.

In one embodiment, the method includes controlling the average value of the applied magnetic flux density along a predetermined axis to maintain a predetermined ratio of frequency-to-composite magnetic flux density. In another embodiment, the frequency of the fluctuations is adjusted to maintain this relationship in which changes in the combined magnetic flux density due to changes in the local magnetic field are detected. Moreover, a combination of these two methods may be used wherein both the frequency and the magnitude of the magnetic field flux density are adjusted to maintaining the predetermined relationship of the present invention.

Hence, the method of the present invention includes the steps of creating and maintaining a predetermined relationship between the frequency of a fluctuating magnetic field to the flux density of the field. In particularly preferred embodiments, the ratio of frequency-to-flux density is determined with reference to the values: a frequency of about 15 to 16 Hertz and an average flux density of about 1.9 to $2.2 \times 10^{-5}$ Tesla. This combination of frequencies and flux densities is particularly useful in stimulating growth factor production at enhanced rates. More preferably, $f_c$ is about 15.3 Hertz and B is about $2 \times 10^{-5}$ Tesla.

In a preferred embodiment of the method of the present invention, the ratio of frequency-to-flux density is determined by selecting a preselected ion present in the interstitial or intracellular fluids associated with the target tissue and tuning the fluctuating composite magnetic flux density to the specific cyclotron resonance frequency for the ion. The preferred ions for stimulating growth factor production are $Ca^{++}$ and $Mg^{++}$. Ions in addition to these ions which may be useful in the present invention are set forth for purposes of illustration, and not limitation, as follows: Hydrogen, $H^+$; lithium $Li^+$; sodium, $Na^+$; chlorine, $Cl^-$; and bicarbonate, $HCO^{-3}$.

Hence, the present invention provides a method for stimulating the production of growth factors which includes the steps of creating a fluctuating magnetic field of predetermined frequency and flux density along an axis projecting through a predetermined volume and positioning a target tissue within this predetermined space such that it is exposed to the fluctuating magnetic field. The predetermined parameters of the fluctuating magnetic field are determined by measuring the net average value of the combined magnetic flux density parallel to the predetermined axis through the tissue, where the combined magnetic field is the sum of the local magnetic field along the predetermined axis and the applied magnetic field. The frequency and/or magnitude of the applied magnetic flux density is then adjusted to produce a combined magnetic field along the axis having a predetermined ratio of frequency to flux density. This predetermined ratio stimulates the production of growth factors at the target site. The tissue is exposed to the fluctuating magnetic field for a duty cycle and a period of time sufficient to properly affect the growth characteristics of the tissue. One advantage of increasing the production of growth factor in and around the tissue to be repaired is that the beneficial effect remains and continues after termination of the fluctuating magnetic field.

The inventive methods of the present invention are further described in the discussion of various apparatus suitable for the practices of the present invention which follows.

Referring now to FIG. 1 of the drawings, growth factor stimulator 20 is shown in position on leg 22 with an injured or damaged area 10 of a subject. It is to be understood that the method of the present invention is suitable for use in stimulating growth factor in a range of living tissue, including but not limited to in vitro cell cultures, animal subjects, or human subjects. Thus, the target tissue which is to be stimulated, is a region of living tissue in a subject or, in other words, in vivo target tissue. It is contemplated that excess growth factor produced by the method of the present invention may be harvested from animal subjects in the conventional manner.

For purposes of this invention, "growth factors" are defined as naturally occurring substances which are produced by a living cell and which increase or stimulate cell growth or proliferation of that cell and/or surrounding cells. Such growth factors generally include such biological active molecules as insulin-like growth factor-II (IGF-II), transforming growth factor $\beta$ (TGF$\beta$), fibroblast growth factor (FGF), and platelet derived growth factor (PDGF).

The area to be treated, in one embodiment injured, damaged, or compromised area 10, may be on the body surface or within the body (i.e., an internal injury). Particularly for animal subjects, whole-body treatment using large coils is contemplated. In the preferred embodiment, the injury may be either soft tissue injury (including, for example, muscles, organs, and the like) or hard tissue (including, for example, ligament, cartilage, and bone). Growth factor stimulator 20 includes two treatment heads 30 and 32 which are positioned on leg 22 in the region of the injured area 10 in the opposed fashion illustrated in FIG. 1. As will be explained more fully, it is important that treatment heads 30 and 32 be placed adjacent the target tissue such that the tissue is within the range of the magnetic flux generated by the treatment heads. Also, although it is preferred that two treatment heads be employed in an opposed fashion as illustrated in FIG. 1, a single treatment head or a plurality of treatment heads greater than two may be suitable in some applications.

Figure 2:
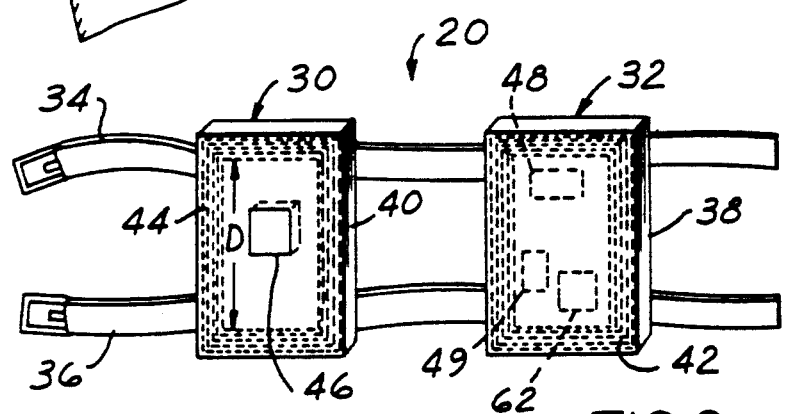
FIG. 2 is a front elevational view of the present invention with two treatment heads having field coils and magnetic field sensing means shown in phantom.

Referring now to FIG. 2 of the drawings, retaining straps 34 and 36 are seen by which growth factor stimulator 20 is preferably secured into position on leg 22. Other securing means may be suitable or desirable in a particular application. It may also be desirable to provide growth factor stimulator 20 as a stationary unit or the like as an alternative to the mobile unit depicted in FIGS. 1–3. Straps or belts 34 and 36 are attached to treatment heads 30 and 32 by any convenient means, preferably in a manner which allows the distance between treatment heads 30 and 32 to be adjusted to obtain the substantially opposed orientation shown in FIG. 1. Hence, it is preferred that straps 30 and 32 permit adjustment sufficient for growth factor stimulator 20 to be used on limbs of various sizes. Treatment heads 30 and 32 should be snugly but comfortably in position to prevent substantial movement relative to the target tissue, illustrated here as injured area 10. In conjunction with conventional plaster or plastic casts, the growth factor stimulator 20 may be integrated directly into the cast architecture or may be mounted on the extension of the cast.

Figure 3:
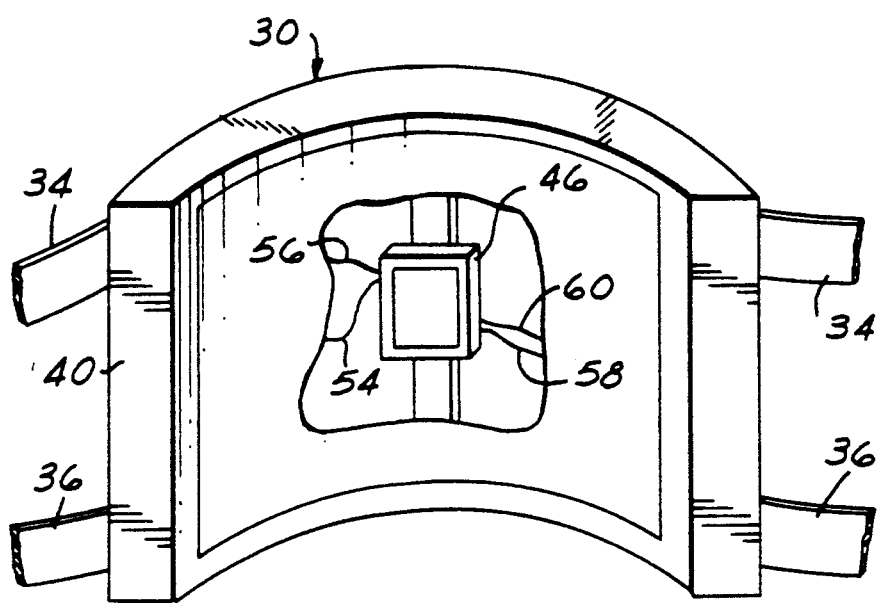
FIG. 3 is a front elevational view of one treatment head of the present invention with the housing broken away to illustrate the magnetic field sensing means.

Referring now to FIGS. 2 and 3, each treatment head 30, 32 includes a housing 38, 40 of a non-magnetic material such as plastic which encloses a field coil 42, 44. In addition, it is preferred that at least one treatment head enclose a magnetic field sensing device 46, such as a Hall-effect device, shown enclosed within housing 40 of treatment head 30. Power source 48 is provided, preferably enclosed within one of the treatment heads. Power source 48 may comprise a dry cell battery or the like. It is preferred that two or more separate power sources be provided to minimize the number of circuit elements required. Housing 38 is also preferably provided with means by which battery 48 can be accessed such as a sliding panel or the like (not shown) to facilitate installation. It may also be suitable to mount battery 48 on the outside of housing 38 or to provide some other external arrangement. While it is an advantage of the present invention to provide a growth factor stimulator which includes a self-contained power source, and thus which is both lightweight and mobile, other power sources such as an ac line source may be used in connection with an ac/dc converter where mobility is not required.

Field coils 44 and 42 are the preferred means by which an applied magnetic field is generated in the present invention. The radius of each field coil 44 and 42, as well as the turns of winding, may vary in accordance with the principles of the present invention. Other electromagnets or possibly permanent magnets may be adapted for use in the present invention. Field coils 44 and 42 are most preferred since they provide a simple means for concentrating magnetic lines of force. Also, since several components may be provided within a single housing, shielding may be employed to prevent undesired interactions between components.

Figure 4:
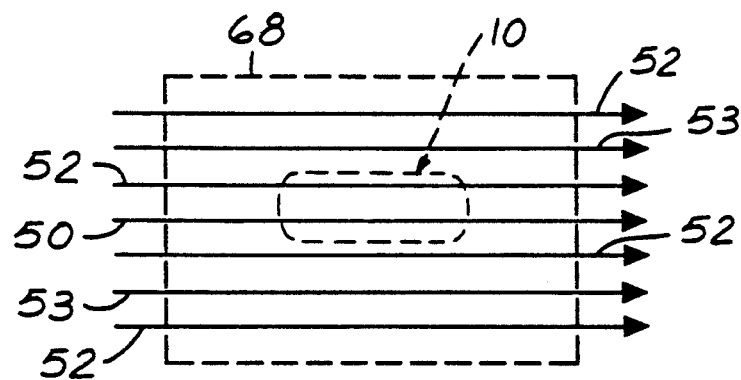
FIG. 4 illustrates the combined magnetic flux of the present invention with changes in intensity over time.

In the most preferred arrangement, the geometry and relative position of field coils 44 and 42 during treatment are such that field coils 44 and 42 operate as Helmholtz coils. Those skilled in the art will thus appreciate that in the most preferred arrangement, field coils 44 and 42 are substantially identical, field-aiding, parallel coaxial coils separated by a distance equal to the radius of each coil. Accordingly, the Helmholtz configuration produces an applied magnetic field in a predetermined space between the coils. Referring to FIG. 4, this predetermined space 68 is occupied by the target tissue, whereby the production of growth factor can be stimulated in accordance with the present invention. This concept will be more fully explained herein. Hence, predetermined space 68 is shown through which magnetic field lines 52 extend parallel to predetermined axis 50. Accordingly, magnetic field lines 52 pass through the target tissue, which is illustrated here as injured area 10.

It will be appreciated that the target tissue will be subject to local magnetic influences As used herein, "local magnetic field" shall be defined as the magnetic influences, including the earth's magnetic field or geomagnetic field, which create a local magnetic flux that flows through the target tissue. "Magnetic flux density" shall be defined in the customary manner as the number of magnetic field lines per unit area of a section perpendicular to the direction of flux. Factors contributing to the local magnetic field in addition to the geomagnetic field may include localized regions of ferromagnetic materials or the like. In one embodiment of the present invention, field coils 42 and 44 are used to create an applied, fluctuating magnetic field which when combined with the local magnetic field parallel to predetermined axis 50 produces a resultant or combined magnetic field having a precisely controlled, predetermined ratio of magnetic flux density to frequency which stimulates the production of growth factor.

Referring now to FIG. 3 of the drawings, magnetic field sensing device or magnetometer 46 is shown in housing 40 with the appropriate leads 54, 56, 58, and 60, by which the field-sensing device is electrically connected to power source 48 and, in one embodiment, to microprocessing means 62, As will be appreciated by those skilled in the art, the Helmholtz configuration of field coils 42 and 44 provides a substantially uniform or equal applied magnetic field in active volume or predetermined space 68 between the coils. Hence, growth factor stimulator 20 allows a substantially uniform applied magnetic field to be applied to the target tissue in predetermined space 68. The direction of the applied magnetic flux defines the direction of predetermined axis 50. That is, the flux of the applied magnetic field is always in the same direction as predetermined axis 50. In the preferred embodiment of the invention, this applied magnetic flux is superimposed on the local magnetic flux in predetermined space 68. The field lines of this local flux component are shown by reference numeral 53.

Magnetometer 46 is positioned in growth factor stimulator 20 to measure the total or composite magnetic flux which passes through predetermined space 68 parallel to predetermined axis 50. It will be understood, then, that magnetometer 46 is provided to measure the composite magnetic field along axis 50. The local field component either augments or decreases the applied magnetic flux unless the local field component is zero. The relatively low applied flux densities and precise predetermined relationships of combined flux density and frequency must be maintained during treatment, notwithstanding the influence of the local magnetic field. This is achieved in essentially two preferred manners which will be explained more fully herein. Thus, magnetometer 46 is provided to determine the magnitude of the magnetic flux density of the local magnetic field. Hence, in one embodiment of the invention, predetermined space 68 is occupied by a region of living tissue of a human or animal subject. Predetermined axis 50 which projects through predetermined space 68 and thus through the target tissue is defined by the relative position of growth factor stimulator 20 with respect to the target tissue. Predetermined axis 50 is in the same direction as the applied magnetic flux generated by field coils 42 and 44 through predetermined space 68. During this procedure, magnetometer 46 measures the total magnetic flux density parallel to predetermined axis 50 which passes through the target tissue. This total or composite magnetic flux density is the sum of the applied component and the local component. The local component may at times be in the same direction as the applied flux and at other times be in directions other than the applied flux. At times the local component may also be zero. These changes in the local component along the axis are produced by changes in the direction of predetermined axis 50 as growth factor stimulator 20 is repositioned such as when an ambulatory patient receiving treatment moves leg 22. Thus at first, the applied flux generated by field coils 42 and 44 may be parallel to a north-south axis, perhaps when the patient faces west. Since the direction of predetermined axis 50 is defined by the direction of the applied flux, in this position, predetermined axis 50 is therefore also in the north-south direction. Later the patient may turn to the north causing a 90 degree rotation of field coils 42 and 44 such that the applied magnetic flux is now parallel to an east-west axis. Accordingly, predetermined axis 50 is then also in the east-west direction. In most cases, the local component will be different in different directions; hence the composite flux measured by magnetometer 46 along predetermined axis 50 will change in response to changes in the position of growth factor stimulator 20 with respect to the local magnetic field. The net average value of magnetic flux density is accordingly regulated to adjust to the change in composite flux. Therefore, growth factor stimulator 20 is preferably a mobile unit which is a significant advantage.

Figure 5:
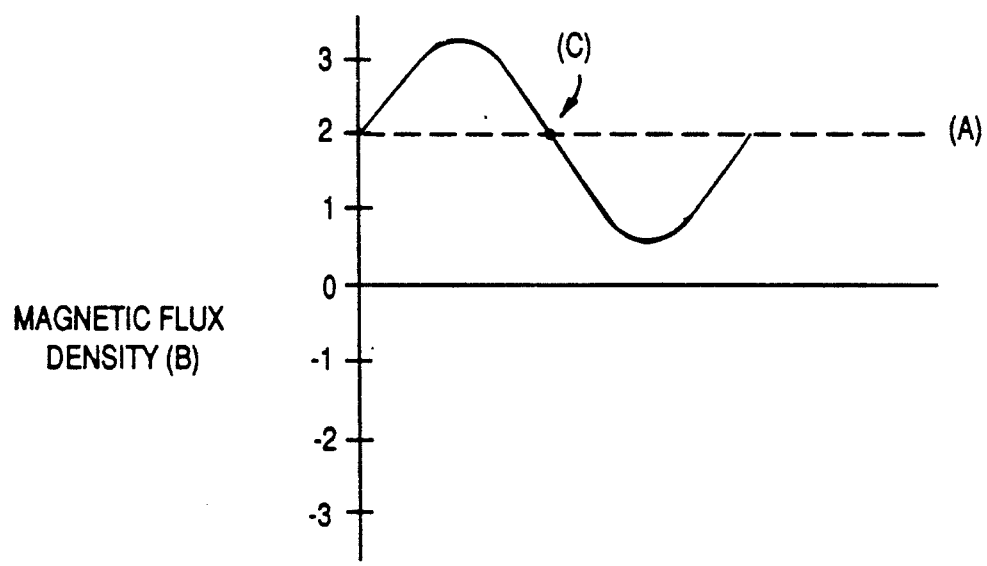
FIG. 5 illustrates the fluctuating, non-zero average value of the combined magnetic flux density.

The unexpected and superior results of the present invention are achieved by creating a fluctuating combined or composite magnetic field having a magnetic flux density parallel to predetermined axis 50, where the combined magnetic flux density along axis 50 is maintained at a predetermined relationship to the frequency of the fluctuations. In this embodiment, the combined magnetic flux density parallel to predetermined axis 50 has a non-zero net average value. As illustrated in FIG. 5 of the drawings, the growth factor-stimulating magnetic field of the present invention can be thought of as a static field having reference level A on which a fluctuating magnetic field is superimposed. It comprises an ac component which varies in amplitude but not direction and a dc reference around which the ac component varies. Reference level A is the non-zero average value of the flux density B. Therefore, it will be understood that the non-zero average or net average value of the composite magnetic flux density along predetermined axis 50 is utilized since the magnitude B of the composite flux density changes at a predetermined rate due to oscillation or fluctuation of the applied magnetic flux. Thus, an average value is utilized which is a non-zero average value illustrated at point C. This reflects that although the composite magnetic flux density along the axis is oscillating at a controlled rate, the composite field is regulated by the intensity of the applied field to ensure that the composite field is always unipolar; that is, the composite field is always in the same direction along predetermined axis 50.

As stated, it has been found that rather precise relationships of the flux density of the combined magnetic field to the frequency of the fluctuations are used in the present invention to provide desired results. These ratios of frequency to composite flux density are found in accordance with the following equation:

$$f_c = (B/2\pi)(q/m)$$

where $f_c$ is the frequency of the combined magnetic field in Hertz, B is the net average value of the magnetic flux density of the combined magnetic field parallel to predetermined axis 50 in Tesla, and q/m is the charge to mass ratio of a preselected ionic species in Coulombs per kilogram. Generally, q/m has a value of from about $5 \times 10^5$ to about $100 \times 10^6$ Coulombs per kilogram and B preferably has a value not in excess of about $5 \times 10^{-4}$ Tesla. To stimulate the production of growth factor, the following frequencies and associated combined magnetic flux densities are preferred: $f_c$ in the range of about 15 to 16 Hertz and B in the range of about $1.9 \times 10^{-5}$ to $2.2 \times 10^{-5}$ Tesla. More preferably, $f_c$ is about 15.3 Hertz and B is about $2 \times 10^{-5}$ Tesla. This value for B corresponds approximately to a 200 milligauss dc and 400 milligauss ac magnetic field.

While the exact mechanism by which growth factor characteristics of the target tissue are affected by the present invention is not fully understood, remarkable results are achieved by tuning the combined field to resonant absorption frequencies of the preselected ion.

Therefore, it will be readily understood by those skilled in the art that tissue growth factor stimulator 20 includes in one aspect a magnetic field generating means for providing an oscillating magnetic field parallel to a predetermined axis. Magnetic growth factor stimulator 20 also preferably includes magnetic field sensing means by which the magnetic flux density parallel to the predetermined axis is measured. A micro-controlling means is also preferably provided in growth factor stimulator 20 by which a predetermined relationship between the magnetic flux density parallel to the predetermined axis and the frequency of the magnetic field oscillation is created and maintained as growth factor stimulator 20 changes orientation with respect to the local magnetic field. Growth factor stimulator 20 is thus used to create, monitor, and adjust a magnetic field of predetermined parameters in predetermined volume 68. While this predetermined relationship is preferably maintained by adjusting the applied flux to compensate for changes in the local field component, alternatively the frequency can be adjusted to preserve the desired ratio.

In use, living tissue is placed within predetermined volume 68 and is then subjected to a fluctuating magnetic field as described for a duty cycle and period of time sufficient to properly influence the growth factor production of the target tissue. This influence will comprise the acceleration of growth factor production and/or the supression of growth factor inhibitors. In this manner, the proliferation and growth of tissue cells is increased. The length of time necessary for successful treatment may vary, depending on the extent of injury. The increased level of growth factor at and near the injured area will, however, have continued beneficial effect after removal of the magnetic field.

As stated, the values for q and m may be determined with reference to a preselected ionic species. It will be known by those skilled in the art that the biochemical milieu of living tissue comprises a mixture of various ions in the intercellular and interstitial fluid. These ions include calcium ions, potassium ions, magnesium ions, sodium ions, chloride ions, phosphate ions, sulfate ions, carbonate ions, bicarbonate ions and the like and various ions formed by the dissociation of amino acids, proteins, sugars, nucleotides and enzymes. Applicants have found that by utilizing the values of charge and mass for a preselected ion in the equation set forth above, which will be recognized by those skilled in the art as the cyclotron resonance relationship solved for $f_c/B$, ratios of frequency to magnetic flux density can be determined which serve to increase growth factor production of living tissue in accordance with the present invention. By using the charge-to-mass ratio of a preselected ion, a specific cyclotron resonance frequency for the ion can be determined. By then tuning tissue growth factor stimulator 20 to maintain a combined magnetic flux density having the proper cyclotron resonance frequency, living tissue containing the preselected ion can be treated to bring about beneficial changes in growth factor production and growth characteristics. The beneficial results of the present invention in this embodiment appear to be achieved when the preselected ion absorbs energy from the magnetic field of the present invention having the desired parameters. It is believed that this increase in energy promotes the transmembrane movement of the preselected ion across the cell membrane of one or more cell types comprising the target tissue. By enhancing the transmembrane movement of preselected ions associated with natural growth factor production in this manner, production of growth factor can be increased by the present invention. For increasing the production of growth factor, it is preferred that the preselected ion is $Ca^{++}$ or $Mg^{++}$; most preferably the preselected ion is $Ca^{++}$.

It will be appreciated by the prior explanation of preferred embodiments of the present invention and from the equation for establishing a cyclotron resonance relationship, that either the frequency of the fluctuating magnetic field or the magnitude or intensity of the magnetic flux density along the predetermined axis, or both the frequency and the intensity of the flux density, can be adjusted to provide a magnetic field within volume 68 which has the desired characteristics. However, as stated, it is preferred to maintain a constant frequency which thus requires that the intensity of the applied magnetic flux density be adjusted to compensate for changes in the local magnetic field in order to maintain a constant ratio of frequency to magnetic flux density. Changes in the local or ambient magnetic field (such as those caused by movement of the subject) which would otherwise cause unwanted deviations in the combined magnetic flux density must be corrected by increasing or decreasing the applied magnetic flux density accordingly. This is most preferably performed by the microcontroller in connection with both the field generating means and the field-sensing device. Alternatively, as stated, if changes in the combined magnetic flux density along the axis will occur due to changes in the orientation of growth factor stimulator 20 with respect to the local magnetic field, the frequency of the oscillations can then be changed so that the preferred ratio is maintained. Once again, it is important to realize that the value of B is the average composite magnetic flux density parallel to the predetermined axis since the magnitude of the flux density changes as the field is oscillated. It be understood that detection of changes in the magnetic field due to changes in the ambient component should be at intervals frequent enough to provide a frequency-to-magnetic field ratio which is substantially constant, notwithstanding the changes in the local field component.

Referring now to FIG. 2 of the drawings, field coils 42 and 44 preferably have up to about 3000 turns or loops of conducting wire each, the diameter d of each loop being preferably up to about 300 centimeters. The number of turns of wire n, the diameter of the coils, the separation of the coils, and the wire gauge are critical only insofar as conventional practice requires constraints on these and other design parameters to allow optimal performance characteristics in achieving predetermined flux densities as required in the preferred practice of the present invention. As stated, other magnetic field generating means may be suitable for use in the present invention and are contemplated as falling within the scope of this invention.

It is also to be understood that the applied magnetic field which results in a combined magnetic flux density along predetermined axis 50 may be produced by a sinusoidal signal or a full-wave rectified signal applied to field coils 42 and 44. It may also be appropriate in some instances to reduce components of the local magnetic field which are not parallel to predetermined axis 50 to zero through the use of additional coils positioned at right angles to treatment heads 30 and 32 to create an opposite but equal field, but this is not deemed necessary. It may also be suitable to reduce the local magnetic field component to zero throughout treatment using additional coils or the like.

Figure 6:
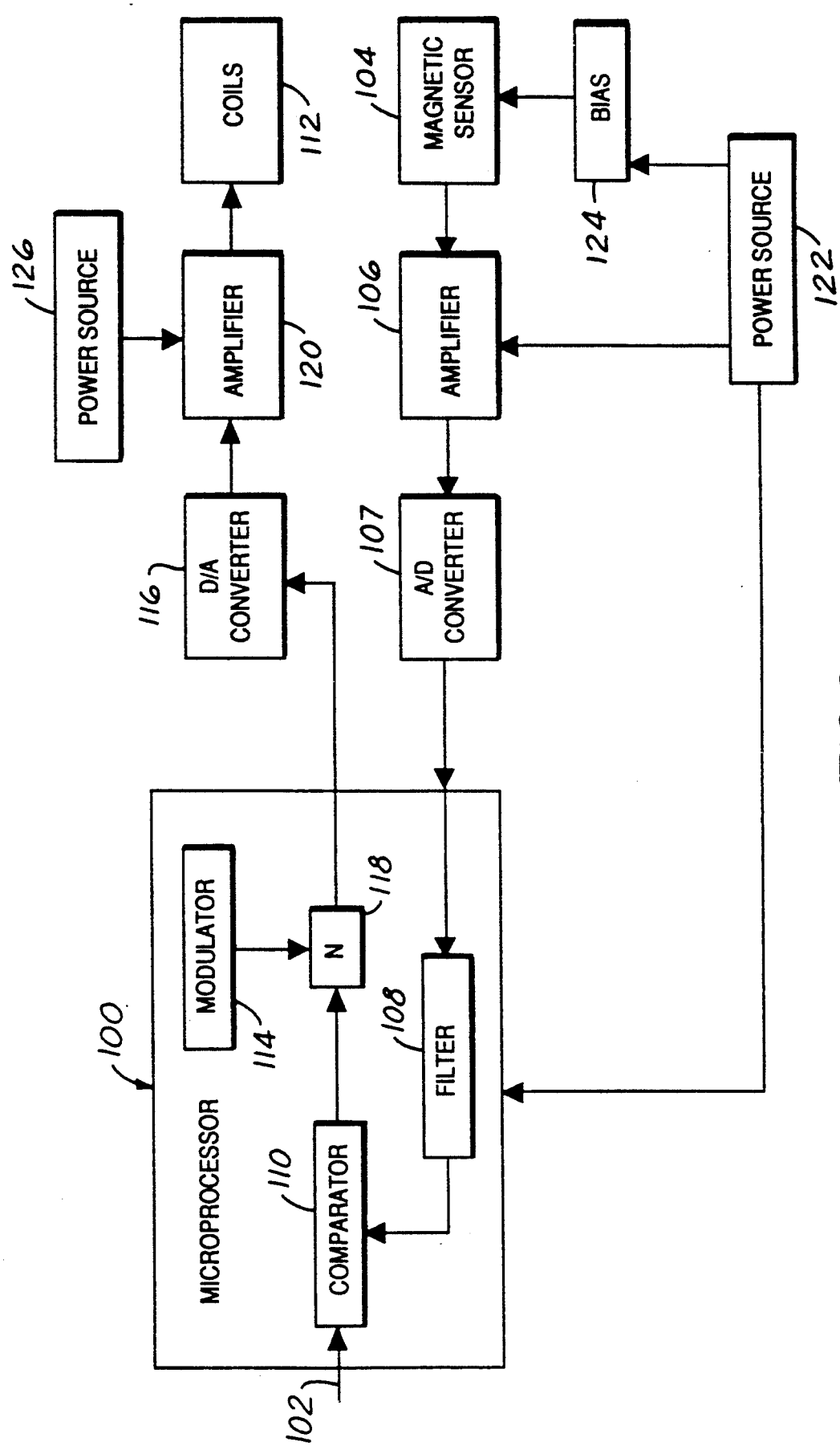
FIG. 6 is a block diagram of an embodiment of the present invention in which the circuit of the inventive apparatus is arbitrarily divided into convenient functional sections.

Referring now to FIG. 6 of the drawings, a block diagram is shown which depicts one suitable arrangement of the circuits of growth factor stimulator 20 in functional segments for carrying out the present invention. Numerous other circuit arrangements may be possible if the principles of the present invention are faithfully observed. Microcontroller or microprocessor 100 is seen by which the composite magnetic field is maintained at a constant predetermined level despite changes in the ambient component as previously described. In this respect, input 102 is provided by which a set point value of the predetermined composite magnetic flux density along a predetermined axis through the target tissue is input into microprocessor 100. As will be shown, the composite field strength is compared to this set point value to generate an error equal to the difference in the set point value and the measured value of the composite magnetic flux density along the axis.

Magnetic field sensor 104 is provided by which the magnitude of the composite field which passes through the target tissue along the axis is measured. It is preferred that magnetic field sensor 104 comprise a Hall-effect device which, as will be known by those skilled in the art, produces an analog signal. The magnetic field sensor 104 constantly monitors the composite magnetic field, sending a signal to microprocessor 100. It will be understood that the output of a Hall-effect magnetic sensor is relatively small; thus, magnetic field sensor amplifier 106 is provided by which the signal from magnetic field sensor 104 is amplified, for example, up to three thousand times its original value. Since a Hall-effect device produces an analog signal, analog-to-digital converter 107 is provided by which the amplified signal from magnetic field sensor 104 is converted to a digital signal which can be used by microprocessor 100. It is preferred that the analog-to-digital converter be provided on-board the microprocessor chip.

As will be appreciated, the amplification of the magnetic field sensor signal may produce an unwanted noise level. Also, sudden changes in the magnetic field intensity may occur which make it difficult to determine the true average value of the composite magnetic flux density. Hence, the signal from analog-to-digital convertor 106 which is input into microprocessor 100 is filtered by software filter 108 to remove shot noise and sudden fluctuations in the composite field detected by magnetic field sensor 104. Although it is preferred that filter 108 comprise software in microprocessor 100, a discrete filter could be used. Accordingly, software filter 108 may be a digital filter, preferably an integrator with a time constant of approximately 0.5 seconds. In other words, the changes in the magnitude of the composite magnetic field which are compensated for by increasing or decreasing the applied field are long-term changes of 0.5 seconds or more which result primarily from changes in the orientation of magnetic growth regulator 20 with respect to the ambient field component. Hence, the time constant of filter 108 would be such that momentary fluctuations are filtered out.

Microprocessor 100 includes logic which calculates the non-zero net average value of the composite magnetic flux density. This non-zero average value is then compared at comparator 110 in microprocessor 100 to the predetermined dc reference or offset value which is input into microprocessor 100 via input 102. It should be noted that this reference value is preferably established by dedicated circuitry in microprocessor 100, although variable input means could be included by which the set point value could be changed. An error statement is then generated defining the difference in the measured value of the composite magnetic flux density and the set point or reference value. Microprocessor 100 then determines the magnitude of the output necessary to drive magnetic field generating coils 112 to bring the composite magnetic flux density back to the set point.

Software field modulator or oscillator 114 is provided by which an ac or fluctuating component is superimposed on the digital output signal which is input into digital-to-analog converter 116. From the previous discussion it will be understood that software field modulator 114 of microprocessor 100 may be preset to a fixed, predetermined frequency to produce the desired predetermined, growth factor-production ratio of frequency-to-magnetic flux density value. Alternatively, the feedback system of the present invention is such that changes in the composite magnetic flux density are measured, whereupon microprocessor 100 determines the necessary change in frequency to maintain the predetermined relationship. Accordingly, software field modulator 114 could produce the requisite ac frequency. It is again preferred that digital-to-analog converter 116 be provided on-board the microprocessor chip. Hence, software field modulator 114 provides the ac component at node 118.

The signal from digital-to-analog converter 116 is fed to voltage-to-current amplifier 120, the output of which drives magnetic field generating coils 112 in the desired manner. Hence, the composite field is held substantially constant despite changes in the ambient component.

While several arrangements of power sources are suitable, it is preferred that power supply 122 be provided to power magnetic field sensor amplifier 106, microprocessor 100 and magnetic field sensor 104, the latter via bias circuitry 124. A separate power source 126 is preferred for voltage to current amplifier 120.

It is also contemplated that the present invention will be useful in systemic treatment of subjects having a growth factor deficiency.

The following examples are provided to further describe and illustrate the present invention and are not intended to limit the scope of the appended claims.

EXAMPLE 1

Human osteosarcoma cells (TE-85 cell line) were placed in tissue culture plates in Dulbecco's modified eagles medium (DMEM). Some of these plates were subject to an oscillating magnetic field at a temperature of 37° C. The magnetic field consisted of a 200 milligauss dc component and a 400 milligauss ac component oscillating at 15.3 Hertz (sine wave). The magnetic flux density was $2.0 \times 10^{-5}$ Tesla. The magnetic field values correspond to the preselected values associated with the $Ca^{++}$ species. Exposure to this oscillating magnetic field continued for 30 minutes. The culture mediums were collected one hour after the termination of the magnetic field exposure. Control samples were treated in the same manner except for exposure to the applied magnetic field.

The collected culture mediums were then added to fresh cultures of TE-85 cells. Cell growth was allowed to continue for 18 hours at a temperature of 37° C. After this time period, an equal amount of $^3H$-thymidine was added to each culture. After three hours, tile culture medium was removed and washed once with phosphate buffered saline. The cell layer was extracted and the radioactivity was measured.

Cell growth or proliferation was equated with the cellular incorporation of $^3H$-thymidine. Such growth should be approximately proportional to the production of growth factor. The following results were obtained:

|  | Average Radioactivity (counts per minute) | No. of samples |
| --- | --- | --- |
| Control (basal) | 7821 ± 1220 | 6 |
| Culture Medium Control (no magnetic field) | 14263 ± 897 | 6 |
| Culture Medium with magnetic field | 18023 ± 1722 | 6 |

The basal control samples consisted of TE-85 cells without any added cultural medium (whether exposed to an applied magnetic field or not). Cell proliferation of the control (cultural medium) was increased 82 percent over that of the basal control. Cell proliferation of the magnetic field exposed sample was increased 130±22 percent over the basal control and 59±11 percent over the cultural medium control.

These results show that the production of growth factor and, in turn, cell proliferation can be significantly increased by the application of a magnetic field as described in the present specification.

EXAMPLE 2

Human bone TE-85 cells were grown in DMEM in the same manner as in Example 1. These cells were exposed to a magnetic field tuned to calcium (200 millgauss dc and 400 millgauss ac at a frequency of 15.3 Hertz) for thirty minutes a day for three days. Samples of the culture medium were collected 24 hours after each exposure and analyzed for IGF-II by radio-receptor assay. The control was treated in the same manner except that it was not subjected to the applied magnetic field. The following results, which are an average of 6 samples, were obtained.

| Time (hrs) | IGF-II (nanograms/ml) Control | Magnetic Field | Percent Change |
| --- | --- | --- | --- |
| 24 | 3.58 | 4.26 | +19 |
| 48 | 5.50 | 5.83 | +6 |
| 72 | 6.27 | 9.55 | +52 |

These results show that the production of the growth factor IGF-II can be significantly increased by the application of a magnetic field as described by this application.

While particular embodiments of the present invention are shown and described herein, the invention is not to be so limited since many modifications may be made, particularly by those skilled in the art, in light of this disclosure. It is contemplated, therefore, by the appended claims, to cover any such modifications as fall within the true spirit and scope of the invention.

What is claimed is:

1. A method for stimulation for production of a growth factor in tissue within a human subject comprising the steps of:
   (1) determining a desired composite magnetic flux having a static field component;
   (2) applying a magnetic flux which fluctuates in intensity to the human subject along an axis;
   (3) sensing the actual composite magnetic flux along the axis in the living tissue, wherein the actual composite magnetic flux includes a component of the fluxuating applied magnetic flux and a component of a naturally existing statetic magnetic flux; and
   (4) comparing the actual composite magnetic flux to the desired composite magnetic flux, determining an error value, and modifying the applied magnetic flux to correct the error value to stimulate the production of a growth factor in said tissue.
   (5) elevating with said applied magnetic flux the level of said growth factor from a first value to a second value at least twenty per cent greater than said first value.

2. A method as defined in claim 1, wherein the growth factor is insulin-like growth factor-II, transforming growth factor $\beta$, fibroblast growth factor, and platelet derived growth factor.

3. A method as defined in claim 1, wherein the stimulation of the production of growth factor in the tissue results in at least a 50 percent increase in cell production in the tissue.

4. A method as defined in claim 1, wherein said growth factor is insulin-like growth factor-II and the stimulation of the production of growth factor in the tissue results in at least a 20 percent increase in the amount of insulin-like growth factor-II produced.

* * * * *